(12) United States Patent
Lehmann et al.

(10) Patent No.: US 7,459,435 B2
(45) Date of Patent: Dec. 2, 2008

(54) TREATMENT OF DISTURBANCES OF IRON DISTRIBUTION

(75) Inventors: Paul Lehmann, Worms (DE); Ralf Roeddiger, Gorxheimertal (DE); Ruth Walter-Matsui, Altenbuseck (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 352 days.

(21) Appl. No.: 10/634,477

(22) Filed: Aug. 4, 2003

(65) Prior Publication Data

US 2004/0110679 A1 Jun. 10, 2004

(30) Foreign Application Priority Data

Aug. 29, 2002 (EP) .................. 02019100

(51) Int. Cl.
*A61K 38/00* (2006.01)
(52) U.S. Cl. ............... 514/12; 514/2; 514/12; 435/7.1
(58) Field of Classification Search ........... None
See application file for complete search history.

(56) References Cited

U.S. PATENT DOCUMENTS

| 4,179,337 | A | 12/1979 | Davis et al. |
|---|---|---|---|
| 4,745,099 | A | 5/1988 | Akamatsu et al. |
| 5,272,071 | A | 12/1993 | Chappel |
| 5,324,650 | A | 6/1994 | Obzansky et al. |
| 5,359,030 | A | 10/1994 | Ekwuribe |
| 5,376,632 | A | 12/1994 | Konings et al. |
| 5,541,158 | A | 7/1996 | Vance et al. |
| 5,641,670 | A | 6/1997 | Treco et al. |
| 5,672,662 | A | 9/1997 | Harris et al. |
| 5,681,811 | A | 10/1997 | Ekwuribe |
| 5,733,761 | A | 3/1998 | Treco et al. |
| 5,981,214 | A | 11/1999 | Skoultchi |
| 5,994,127 | A | 11/1999 | Selden et al. |
| 6,333,306 | B1 | 12/2001 | Lehmann et al. |
| 6,340,742 | B1 | 1/2002 | Burg et al. |
| 6,372,715 | B1 | 4/2002 | Kaltwasser et al. |
| 6,440,932 | B1 | 8/2002 | Lehmann et al. |
| 6,528,313 | B1 | 3/2003 | Le Mouellic et al. |
| 6,583,272 | B1 | 6/2003 | Bailon |
| 2002/0065214 | A1 | 5/2002 | Iaina et al. |
| 2002/0115833 | A1 | 8/2002 | Burg et al. |
| 2002/0160956 | A1 | 10/2002 | Lehmann et al. |

FOREIGN PATENT DOCUMENTS

| DE | 3924705 | 1/1991 |
|---|---|---|
| EP | 0205564 | 12/1986 |
| EP | 0286439 | 10/1988 |
| EP | 0411678 | 2/1991 |
| EP | 539167 | 4/1993 |
| EP | 584876 | 3/1994 |
| EP | 605963 | 7/1994 |
| EP | 640619 | 3/1995 |
| EP | 1064951 | 1/2001 |
| WO | WO 90/11354 | 10/1990 |
| WO | WO 91/06667 | 5/1991 |
| WO | WO 91/09955 | 7/1991 |
| WO | WO 92/16555 | 10/1992 |
| WO | WO 93/09222 | 5/1993 |
| WO | WO 93/25212 | 12/1993 |
| WO | WO 94/12650 | 6/1994 |
| WO | WO 94/20069 | 9/1994 |
| WO | WO 94/28024 | 12/1994 |
| WO | WO 95/11924 | 5/1995 |
| WO | WO 95/31560 | 11/1995 |
| WO | WO 97/04796 | 2/1997 |
| WO | WO 97/09996 | 3/1997 |
| WO | WO 98/32466 | 7/1998 |
| WO | WO 98/41226 | 9/1998 |
| WO | WO 01/02017 | 1/2001 |
| WO | WO 01/87329 | 11/2001 |
| WO | WO 03/025583 A2 | 3/2003 |

OTHER PUBLICATIONS

Bosman et al., Diabetes Care, vol. 24, pp. 495-499, 2001.*
Silverberg et al., Nephrol. Dial. Transplant., vol. 18 (1), pp. 141-146, 2003.*
Yamaguchi et al., The Journal of Biological Chemistry, vol. 266, No. 30, pp. 20434-20439, 1991.*
March J., Advanced Organic Chemistry, McGraw-Hill, 1977, pp. 375-376.
Grasetti, D. R. & Murray, J. F., J. Appl. Biochem. Biotechnol. 119, pp. 41-49, 1967.
Morpurgo M. et al., J. Bioconj. Chem. (1996) vol. 7, pp. 363-368.
Hermanson, G. T. Bioconjugate Techniques Academic Press, San Diego (1996) pp. 147-148.
Annable, et al. Bull. Wld. Hlth. Org. (1972) vol. 47 pp. 99-112.
Abstract corresponding to WO 90/11354 (B25).
Thomas Christian et al, Clinical Chemistry, Amer. Assoc. for Clin. Chem. vol. 48(7) (2002) pp. 106-1076.
Peeters H R M et al, Rheumatology International, vol. 18, (1999) pp. 201-206.
Devita MV, et al., Clin Nephrol, 60(5):335-40 (2003).
Abstract corresponding to WO 90/11354 (B25), 1990.
P. Lehmann, M. Volkmann, J. Lotz, A. Baldauf, R. Roeddiger, poster presented at the AACC/CSCC, Annual Meeting, Jul. 29-Aug. 2, 2001, Chicago Illinois.
Abstract corresponding to DE 3924705, 1991.
Grützmacher P., et al., *Clinical Nephrology*, vol. 38, pp. 92-97, 1992.
Wick, M.; Pinggera, W.; Lehmann, P., *Eisenstoffwechsel Diagnostik und Therapie der Anümien*, 3rd edition, Springer, Wien, NY, pp. 5-14, 38-55, 65-80, 94-98, Sep. 1996.

(Continued)

*Primary Examiner*—Hope A Robinson
(74) *Attorney, Agent, or Firm*—George W. Johnston; Dennis P. Tramaloni; Samuel H. Megerditchian

(57) ABSTRACT

A method of, and pharmaceutical composition for, treating disturbances of iron distribution in diabetes using erythropoietin are disclosed.

20 Claims, 1 Drawing Sheet

OTHER PUBLICATIONS

Sunder-Plassmann G., et al., *Journal of the American Society of Nephrology*, 5, (3), pp. 478 (1994).

Gasche C., et al., *Dig. Dis. Sci.*, 39, (9) pp. 1930-1934 (1994).

Sunder-Plassmann G., et al., *Nephrology Dialysis Transplantation*, 10, (11), pp. 2070-2076 (1995).

Mercuriali F. et al., Erythropoiesis: *New Dimensions in the Treatment of Anaemia*, 6/3, pp. 67-76, (1995).

Sunder-Plassmann G., et al., *Nephrology Dialysis Transplantation*, 11, (9), pp. 1797-1802, (1996).

Taylor, J. E., et al., *Nephrology Dialysis Transplantation*, 11, (6), pp. 1079-1083, (1996).

MacDougall (1994) Monitoring of Iron Status & Iron Supplementation in Patients Treated with Erythropoietin. *Current Opinion in Nephrology & Hypertension* 3(6) pp. 620-625.

Taylor et al. (1996) Regular low-dose Intravenous Iron Therapy Improves Response to Erythropoietin in Haemodialysis Patients. *Nephrology, Dialysis, & Transplantation* 11(6) pp. 1079-1083.

Means, Jr. (1995) Erythropoietin in the Treatment of Anemia in Chronic Infectious, Inflammatory, & Malignant Diseases. *Current Opinion in Hematology* 2(3) pp. 210-213.

Adamson (1996) Erythropoietin, Iron Metabolism, & Red Blood Cell Production. *Seminars In Hematology* 33(2) pp. 5-9.

Mercuriali & Inghilleri (1995) Iron Administration to Optimise the Effect of r-HuEPO in the Surgical Setting. Erythropoiesis: *New Dimensions in the Treatment of Anemia* 6(3) pp. 67-76.

Pincus et al. (Aug. 1990) Multicultural Study of Recombinant Human Erythropoietin in Correction of Anemia in Rheumatoid Arthritis. *The American Journal of Medicine* 89(2) pp. 161-168.

Lawrence Tim Goodnough, et al., "Parenteral Iron and Recombinant Human Erythropoietin Therapy to Stimulate Erythropoiesis in Patients Undergoing Repair of His Fracture,"Hematology, vol. 1, pp. 163-166 (1996).

C. Breymann, et al., "Recombinant human erythropoietin in combination with parenteral iron in the treatment of postpartum anaemia," European Journal of Clinical Investigation, vol. 26, No. 2, pp. 123-130(8), Feb. 1996.

US 5,733,746, 03/1998, Treco et al. (withdrawn)

* cited by examiner

SEQ ID NO: 1

Ala Pro Pro Arg Leu Ile Cys Asp Ser Arg$^{10}$ Val Leu Glu Arg Tyr Leu Leu Glu Ala Lys$^{20}$

Glu Ala Glu Asn Ile Thr Thr Gly Cys Ala$^{30}$ Glu His Cys Ser Leu Asn Glu Asn Ile Thr$^{40}$
Val Pro Asp Thr Lys Val Asn Phe Tyr Ala$^{50}$ Trp Lys Arg Met Glu Val Gly Gln Gln Ala$^{60}$
Val Glu Val Trp Gln Gly Leu Ala Leu Leu$^{70}$ Ser Glu Ala Val Leu Arg Gly Gln Ala Leu$^{80}$
Leu Val Asn Ser Ser Gln Pro Trp Glu Pro$^{90}$ Leu Gln Leu His Val Asp Lys Ala Val Ser$^{100}$
Gly Leu Arg Ser Leu Thr Thr Leu Leu Arg$^{110}$ Ala Leu Gly Ala Gln Lys Glu Ala Ile Ser$^{120}$
Pro Pro Asp Ala Ala Ser Ala Ala Pro Leu$^{130}$ Arg Thr Ile Thr Ala Asp Thr Phe Arg Lys$^{140}$
Leu Phe Arg Val Tyr Ser Asn Phe Leu Arg$^{150}$ Gly Lys Leu Lys Leu Tyr Thr Gly Glu Ala$^{160}$
Cys Arg Thr Gly Asp$^{165}$

TREATMENT OF DISTURBANCES OF IRON DISTRIBUTION

PRIORITY TO RELATED APPLICATIONS

This application claims foreign priority to EP 02019100.3, filed Aug. 29, 2002.

FIELD OF THE INVENTION

The present invention relates to a new use of erythropoietin, in the treatment of disturbances of iron distribution in diabetes.

BACKGROUND OF THE INVENTION

Various diseases are known in which the metabolism of iron is not normal. In anemia, not enough blood can be formed due to an overall lack of iron in the body. Another metabolic condition relating to iron disturbance is hemochromatosis, in which the overall concentration of iron in the body is higher than normal. This leads to various deleterious conditions, including the possible destruction of organs.

Disturbances of iron distribution differ from the above described anemia and hemochromatosis because the overall concentration of iron in the body is normal. However, excess iron is accumulated in various organs and can lead to damage and even destruction of these organs. On the other hand, the use of the iron which is present in normal quantities in the formation of blood is impaired, leading to secondary effects which are comparable to those related to anemia.

Until now it was not known that patients suffering from diabetes have a high probability to be affected by disturbances of iron distribution. Disturbances of iron distribution can be diagnosed by various parameters which are commonly used in the diagnosis of the iron status. Based on measurements of ferritin and soluble transferrin receptor it is possible to assess whether the overall concentration of iron in a diabetic patient is normal. If this is the case, then a lowered concentration of Hemoglobin in reticulocytes is an indicator for disturbances of iron distribution. Another indicator is a continuously/prolonged elevated concentration of C-reactive protein (CRP) in patients suffering from diabetes and exhibiting a normal overall iron concentration. A method for diagnosing disturbances of iron distribution has been described by P. Lehmann, M. Volkmann, J. Lotz, A. Baldauf, R. Roeddiger, poster presented at the AACC/CSCC, Annual Meeting, Jul. 29-Aug. 2, 2001, Chicago, Ill.

SUMMARY OF THE INVENTION

So far, no treatment has yet been suggested for diabetic patients suffering from disturbances in iron distribution. The problem underlying the present invention is therefore to provide a treatment for disturbances of iron distribution in diabetes in order to minimize or suppress the above mentioned disadvantages. It has surprisingly been found that erythropoietin has a beneficial effect on disturbances of iron distribution in diabetes.

The problem is therefore solved, according to the present invention, by providing erythropoietin for the use in the treatment of disturbances of iron distribution in diabetes.

DETAILED DESCRIPTION OF THE INVENTION

Unless otherwise indicated the following definitions are set forth to illustrate and define the meaning and scope of the various terms used to describe the invention herein.

The term "lower-alkyl" as used herein means a linear or branched alkyl group having from one to six carbon atoms. Examples of lower-alkyl groups include methyl, ethyl and isopropyl, preferably methyl.

The term "lower-alkoxy" as used herein means a group R'—O—, wherein R' is a lower-alkyl as described above.

The term "disturbances of iron distribution in diabetes" refers to a disturbance of iron distribution which occurs in patients suffering from diabetes. The disturbance of iron distribution can e.g. be characterized as described above. Particularly, a disturbance of iron distribution is characterized by the following parameters: concentration of soluble transferrin receptor [mg/L] divided by log(concentration of ferritin [µg/L]) is smaller than 3.5 and simultaneously concentration of C-reactive protein is above 5 mg/L.

The term "erythropoietin" or "erythropoietin protein" refers to a protein with the in vivo biological activity of causing bone marrow cells to increase production of reticulocytes and red blood cells and selected from the group consisting of human erythropoietin and analogs which are defined below.

The term "pegylated erythropoietin (Peg-EPO or PEG-EPO)" refers to an erythropoietin protein which is covalently linked with one to three polyethylene derivatives as described below.

DESCRIPTION OF DRAWINGS

FIG. 1: Primary structure of human EPO (165 amino acids) (SEQ ID NO:1).

In more detail, the present invention relates to the use of erythropoietin in the manufacture of a medicament for the treatment of disturbances of iron distribution in diabetes. In a preferred embodiment, the invention relates to a use as defined above, wherein diabetes is non insulin dependant diabetes mellitus.

The present invention is especially useful for the preparation of pharmaceutical compositions comprising erythropoietin as pharmaceutically active ingredient. The term "erythropoietin" or "erythropoietin protein" or "EPO" is as follows: particularly the terms refer to a glycoprotein, e.g. the human erythropoietin, e.g. having the amino acid sequence set out in (SEQ ID NO: 1) or an amino acid sequence substantially homologous thereto, whose biological properties relate to the stimulation of red blood cell production and the stimulation of the division and differentiation of committed erythroid progenitors in the bone marrow. As used herein, these terms include such proteins modified deliberately, as for example, by site directed mutagenesis or accidentally through mutations. These terms also include analogs having from 1 to 6 additional sites for glycosylation, analogs having at least one additional amino acid at the carboxy terminal end of the glycoprotein, wherein the additional amino acid includes at least one glycosylation site, and analogs having an amino acid sequence which includes a rearrangement of at least one site for glycosylation. These terms include both natural and recombinantly produced human erythropoietin. In a preferred embodiment of the present invention, the erythropoietin protein is a human erythropoietin.

As set out in detail below, the preparation and purification of EPO are well known in the art. By erythropoietin is meant the natural or recombinant protein, preferably human, e.g. epoetin alfa or epoetin beta, as obtained from any conventional source such as tissues, protein synthesis, cell culture with natural or recombinant cells. Any protein having the activity of erythropoietin, such as muteins or otherwise modified proteins, is encompassed. In a preferred embodiment of the present invention, the erythropoietin protein is epoetin alfa or epoetin beta. Recombinant EPO may be prepared via expression in CHO-, BHK- or HeLa cell lines, by recombinant DNA technology or by endogenous gene activation. Expression of proteins, including, by endogenous gene activation, is well known in the art and is disclosed, for example in U.S. Pat. Nos. 5,733,761, 5,641,670, 5,733,746, 5,994,127 (WO 93/09222), U.S. Pat No. 5,733,761 (WO 94/12650), U.S. Pat No. 5,641,670 (WO 95/31560), U.S. Pat. No. 6,528, 313 (WO 90/11354), U.S. Pat No. 5,981,214 (WO 91/06667) and U.S. Pat No 5,272,071 (WO 91/09955), the contents of each of which are incorporated herein by reference. The use as defined above, wherein the erythropoietin protein is expressed by endogenous gene activation, is preferred. The preferred EPO species for the preparation of erythropoietin glycoprotein products are human EPO species. More preferably, the EPO species is the human EPO having the amino acid sequence set out in SEQ ID NO:1. A preferred embodiment of the present invention therefore relates to the use as described above, wherein the erythropoietin protein has the amino acid sequence of SEQ ID NO:1.

Further, erythropoietin may be a glycoprotein analog having from 1 to 6 additional sites for glycosylation. Therefore, the present invention also relates to the use as described before, wherein the erythropoietin protein has the sequence of human erythropoietin modified by the addition of from 1 to 6 glycosylation sites. Glycosylation of a protein, with one or more oligosaccharide groups, occurs at specific locations along a polypeptide backbone and greatly affects the physical properties of the protein such as protein stability, secretion, subcellular localization, and biological activity. Glycosylation is usually of two types. O-linked oligosaccharides are attached to serine or threonine residues and N-linked oligosaccharides are attached to asparagine residues. One type of oligosaccharide found on both N-linked and O-linked oligosaccharides is N-acetylneuraminic acid (sialic acid), which is a family of amino sugars containing 9 or more carbon atoms. Sialic acid is usually the terminal residue on both N-linked and O-linked oligosaccharides and, because it bears a negative charge, confers acidic properties to the glycoprotein. Human erythropoietin, having 165 amino acids, contains three N-linked and one O-linked oligosaccharide chains which comprise about 40% of the total molecular weight of the glycoprotein. N-linked glycosylation occurs at asparagine residues located at positions 24, 38, and 83 and O-linked glycosylation occurs at a serine residue located at position 126. The oligosaccharide chains are modified with terminal sialic acid residues. Enzymatic removal of all sialic acid residues from the glycosylated erythropoietin results in loss of in vivo activity but not in vitro activity because sialylation of erythropoietin prevents its binding, and subsequent clearance, by hepatic binding protein.

The term "erythropoietin" includes analogs of human erythropoietin with one or more changes in the amino acid sequence of human erythropoietin which result in an increase in the number of sites for sialic acid attachment. These glycoprotein analogs may be generated by site-directed mutagenesis having additions, deletions, or substitutions of amino acid residues that increase or alter sites that are available for glycosylation. Glycoprotein analogs having levels of sialic acid greater than those found in human erythropoietin are generated by adding glycosylation sites which do not perturb the secondary or tertiary conformation required for biological activity. The glycoproteins of the present invention also include analogs having increased levels of carbohydrate attachment at a glycosylation site which usually involve the substitution of one or more amino acids in close proximity to an N-linked or O-linked site. The glycoproteins of the present invention also include analogs having one or more amino acids extending from the carboxy terminal end of erythropoietin and providing at least one additional carbohydrate site. The erythropoietin proteins of the present composition also include analogs having an amino acid sequence which includes a rearrangement of at least one site for glycosylation. Such a rearrangement of glycosylation site involves the deletion of one or more glycosylation sites in human erythropoietin and the addition of one or more non-naturally occurring glycosylation sites. Increasing the number of carbohydrate chains on erythropoietin, and therefore the number of sialic acids per erythropoietin molecules may confer advantageous properties such as increased solubility, greater resistance to proteolysis, reduced immunogenecity, increased serum half-life, and increased biological activity. Erythropoietin analogs with additional glycosylation sites are disclosed in more detail in European Patent Application 640 619, to Elliot published Mar. 1, 1995.

In a preferred embodiment, the pharmaceutical composition of the present invention comprises erythropoietin proteins with an amino acid sequence which includes at least one additional site for glycosylation such as, but not limited to, erythropoietins comprising the sequence of human erythropoietin modified by a modification selected from the following:

$Asn^{30}Thr^{32}$;
$Asn^{51}Thr^{53}$;
$Asn^{57}Thr^{59}$;
$Asn^{69}$;
$Asn^{69}Thr^{71}$;
$Ser^{68}Asn^{69}Thr^{71}$;
$Val^{87}Asn^{88}Thr^{90}$;
$Ser^{87}Asn^{88}Thr^{90}$;
$Ser^{87}Asn^{88}Gly^{89}Thr^{90}$(SEQ ID NO: 2);
$Ser^{87}Asn^{88}Thr^{90}Thr^{92}$;
$Ser^{87}Asn^{88}Thr^{90}Ala^{162}$;
$Asn^{69}Thr^{71}Ser^{87}Asn^{88}Thr^{90-}$;
$Asn^{30}Thr^{32}Val^{87}Asn^{88}Thr^{90-}$;
$Asn^{89}Ile^{90}Thr^{91}$;
$Ser^{87}Asn^{89}Ile^{90}Thr^{91}$;
$Asn^{136}Thr^{138}$;
$Asn^{138}Thr^{140}$;
$Thr^{125}$; and
$Pro^{124}Thr^{125}$.

The notation used herein for modification of amino acid sequence means that the position(s) of the corresponding unmodified protein (e.g. hEPO of SEQ ID NO:1) indicated by the superscripted number(s) is changed to the amino acid(s) that immediately precede the respective superscripted number(s).

The erythropoietin protein may also be an analog having at least one additional amino acid at the carboxy terminal end of the glycoprotein, wherein the additional amino acid includes at least one glycosylation site. The additional amino acid may comprise a peptide fragment derived from the carboxy terminal end of human chorionic gonadotropin. Preferably, the glycoprotein is an analog selected from the group consisting of (a) human erythropoietin having the amino acid sequence, Ser Ser Ser Ser Lys Ala Pro Pro Pro Ser Leu Pro Ser Pro Ser Arg Leu Pro Gly Pro Ser Asp Thr Pro Ile Leu Pro Gln (SEQ ID NO: 3), extending from the carboxy terminus; (b) the analog in (a) further comprising $Ser^{87}$ $Asn^{88}$ $Thr^{90}$ EPO; and (c) the analog in (a) further comprising $Asn^{30}$ $Thr^{32}$ $Val^{87}$ $Asn^{88}$ $Thr^{90}$ EPO.

The erythropoietin protein may also be an analog having an amino acid sequence which includes a rearrangement of at least one site for glycosylation. The rearrangement may comprise a deletion of any of the N-linked carbohydrate sites in human erythropoietin and an addition of an N-linked carbohydrate site at position 88 of the amino acid sequence of human erythropoietin. Preferably, the glycoprotein is an analog selected from the group consisting of $Gln^{24}$ $Ser^{87}$ $Asn^{88}$ $Thr^{90}$ EPO; $Gln^{38}$ $Ser^{87}$ $Asn^{88}$ $Thr^{90}$ EPO; and $Gln^{83}$ $Ser^{87}$ $Asn^{88}$ $Thr^{90}$ EPO. A further analog is darbepoetin alfa. A preferred erythropoietin protein in the use described before is darbepoietin alfa.

More particularly, the erythropoietin protein of the present pharmaceutical composition as described above may also include pegylated derivatives thereof. Pegylated derivatives of erythropoietin and their preparation are known in the art and described for example in WO 01/02017, EP-A-1064951, EP-A-539,167, EP-A-605,963, WO 93/25212, WO 94/20069, WO 95/11924, U.S. Pat. No. 5,56, EP-A-584,876, WO 92/16555, WO 94/28024, WO 97/04796, U.S. Pat. Nos. 5,359,030 and 5,681,811, U.S. Pat. No. 4,179,337, Japanese Patent, WO 98/32466, U.S. Pat. Nos. 5,324,650 and 6,583,272 B1.

In a preferable embodiment of the invention, the erythropoietin protein used in the described method and compositions is pegylated.

Accordingly, the present invention also refers to the use as described above, wherein the erythropoietin protein is a conjugate, said conjugate comprising an erythropoietin protein as described above having at least one free amino group and having the in vivo biological activity of causing bone marrow cells to increase production of reticulocytes and red blood cells and selected from the group consisting of human erythropoietin and analogs thereof which have a sequence of human erythropoietin modified by the addition of from 1 to 6 glycosylation sites or a rearrangement of at least one glycosylation site; said erythropoietin being covalently linked to "n" poly(ethylene glycol) groups of the formula —CO—$(CH_2)_x$—$(OCH_2CH_2)_m$—OR with the —CO (i.e. carbonyl) of each poly(ethylene glycol) group forming an amide bond with one of said amino groups; wherein R is lower-alkyl; x is 2 or 3; m is from about 450 to about 900; n is from 1 to 3; and n and m are chosen so that the molecular weight of the conjugate minus the erythropoietin protein is from 20 kilodaltons to 100 kilodaltons. This invention further provides pharmaceutical compositions containing conjugates described herein in which the percentage of conjugates in which n is 1 is at least ninety percent, preferably at least ninety-two percent, ore preferably ninety-sex percent of all conjugates of the composition.

More specifically the above conjugates may be represented by formula (I)

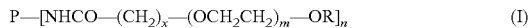

wherein P is the residue of an erythropoietin protein as described herein, (i.e. without the free amino group or amino groups which form an amide linkage with the carbonyl shown in Formula I), having the in vivo biological activity of causing bone marrow cells to increase production of reticulocytes and red blood cells; and wherein R is lower-alkyl; x is 2 or 3; m is from about 450 to about 900; n is from 1 to 3; and n and m are chosen so that the molecular weight of the conjugate minus the erythropoietin glycoprotein is from 20 kilodaltons to 100 kilodaltons. In accordance with this invention, R is any lower-alkyl. Conjugates in which R is methyl are preferred.

The symbol "m" represents the number of ethylene oxide residues ($OCH_2CH_2$) in the poly(ethylene oxide) group. A single PEG (polyethylene glycol) subunit of ethylene oxide has a molecular weight of about 44 daltons. Thus, the molecular weight of the conjugate (excluding the molecular weight of the EPO) depends on the number "m". In the conjugates of this invention "m" is from about 450 to about 900 (corresponding to a molecular weight of about 20 kDa to about 40 kDa), preferably from about 650 to about 750 (corresponding to a molecular weight of about 30 kDa). The number m is selected such that the resulting conjugate of this invention has a physiological activity comparable to unmodified EPO, which activity may represent the same as, more than, or a fraction of the corresponding activity of unmodified EPO. A molecular weight of "about" a certain number means that it is within a reasonable range of that number as determined by conventional analytical techniques. The number "m" is selected so that the molecular weight of each poly(ethylene glycol) group covalently linked to the erythropoietin glycoprotein is from about 20 kDa to about 40 kDa, and is preferably about 30 kDa.

In the conjugates of this invention, the number "n is the number of poly(ethylene glycol) groups covalently bound to free amino groups (including ε-amino groups of a lysine amino acid and/or the amino-terminal amino group) of an erythropoietin protein via amide linkage(s). A conjugate of this invention may have one, two, or three PEG groups per molecule of EPO. "n" is an integer ranging from 1 to 3, preferably "n" is 1 or 2, and more preferably "n" is 1. A preferred conjugate of the conjugates described above comprises compounds wherein x is 2, m is 650 to 750, n is 1 and R is methyl.

The compound of formula (I) can be prepared from the known polymeric material:

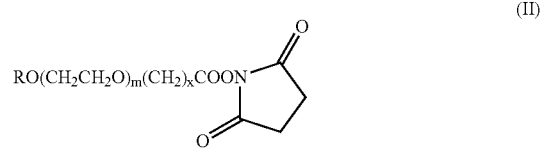

in which R and m are as described above, by condensing the compound of Formula II with the erythropoietin glycoprotein. Compounds of formula (II) in which x is 3 are alpha-lower-alkoxy, butyric acid succinimidyl esters of poly(ethylene glycol) (lower-alkoxy-PEG-SBA). Compounds of formula (II) in which x is 2 are alpha-lower-alkoxy, propionic acid succinimidyl esters of poly (ethylene glycol) (lower-alkoxy-PEG-SPA). Any conventional method of reacting an activated ester with an amine to form an amide can be utilized. In the reaction described above, the exemplified succinimidyl ester is a leaving group causing the amide formation. The use of succinimidyl esters such as the compounds of formula II to produce conjugates with proteins are disclosed in U.S. Pat. No. 5,672,662, issued Sep. 30, 1997 (Harris, et al.).

Human EPO contains nine free amino groups, the amino-terminal amino group plus the ε-amino groups of 8 lysine residues. When the pegylation reagent was combined with a SBA compound of Formula II, it has been found that at pH 7.5, a protein:PEG ratio of 1:3, and a reaction temperature of from 20-25° C., a mixture of mono-, di-, and trace amounts of the tri-pegylated species were produced. When the pegylation reagent was a SPA compound of Formula II, at similar conditions except that the protein:PEG ratio was 1:2, primarily the mono-pegylated species is produced. The pegylated EPO can be administered as a mixture, or as the cation exchange chromatography separated different pegylated species. By manipulating the reaction conditions (e.g., ratio of reagents, pH, temperature, protein concentration, time of reaction etc.), the relative amounts of the different pegylated species can be varied.

A further preferred embodiment of the present invention relates to the use as defined above, wherein the erythropoietin protein is a conjugate, said conjugate comprising an erythropoietin protein as defined above having at least one free amino group and having the in vivo biological activity of causing bone marrow cells to increase production of reticulocytes and red blood cells and selected from the group consisting of human erythropoietin protein and analogs thereof which have the primary structure of human erythropoietin protein modified by the addition of from 1 to 6 glycosylation sites; said erythropoietin protein being covalently linked to from one to three lower-alkoxy poly(ethylene glycol) groups, each poly(ethylene glycol) group being covalently linked to the erythropoietin protein via a linker of the formula —C(O)—X—S—Y— with the C(O) of the linker forming an amide bond with one of said amino groups, X is —(CH$_2$)$_k$— or —CH$_2$(O—CH$_2$—CH$_2$)$_k$—, k is from 1 to 10, Y is

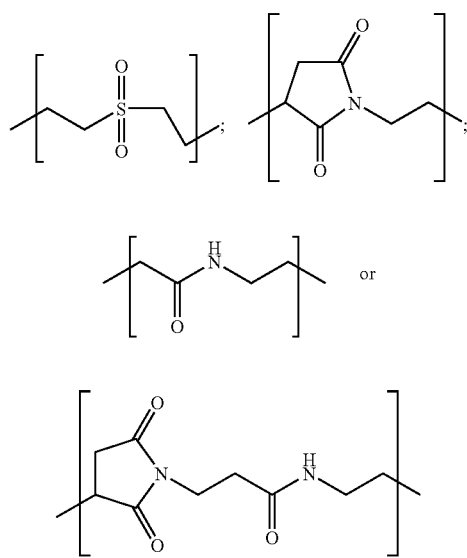

the average molecular weight of each poly(ethylene glycol) moiety is from about 20 kilodaltons to about 40 kilodaltons, and the molecular weight of the conjugate is from about 51 kilodaltons to about 175 kilodaltons.

This erythropoietin species may also be represented by formula (III)

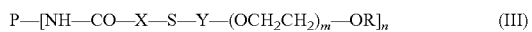

wherein R may be any lower-alkyl. A preferred lower-alkyl is methyl. X may be —(CH$_2$)$_k$— or —CH$_2$(O—CH$_2$—CH$_2$)$_k$—, wherein k is from 1 to about 10. Preferably, k is from 1 to about 4, more preferably, k is 1 or 2. Most preferably, X is —(CH$_2$).

In Formula 1, Y is selected from

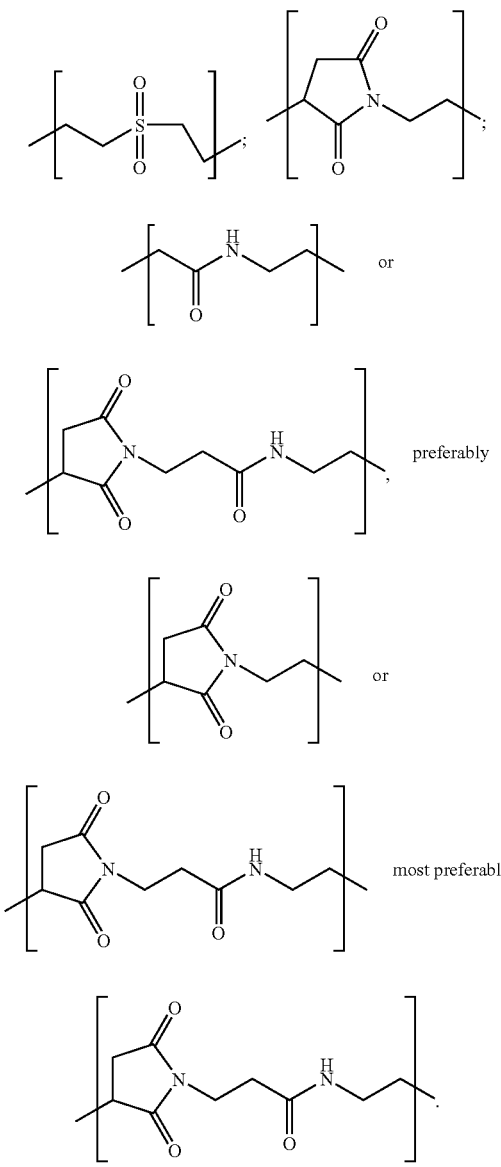

In formula (III), the number m is selected such that the resulting conjugate of formula (III) has a physiological activity comparable to unmodified EPO, which activity may represent the same as, more than, or a fraction of the corresponding activity of unmodified EPO. m represents the number of ethylene oxide residues in the PEG unit. A single PEG subunit of —(OCH$_2$CH$_2$)— has a molecular weight of about 44 daltons. Thus, the molecular weight of the conjugate (excluding the molecular weight of the EPO) depends on the number m. A molecular weight of "about" a certain number means that it is within a reasonable range of that number as determined by conventional analytical techniques. m is an integer ranging from about 450 to about 900 (corresponding to a molecular weight of from 20 to 40 kDa), preferably m is from about 550 to about 800 (about 24 to 35 kDa), and most preferably m is from about 650 to about 700 (about 29 to about 31 kDa).

In formula (III), the number n is the number of ε-amino groups of a lysine amino acid in an erythropoietin protein covalently bound to a PEG unit via an amide linkage. A conjugate of this invention may have one, two, or three PEG units per molecule of EPO. n is an integer ranging from 1 to 3, preferably n is 1 or 2, and more preferably n is 1.

Preferred erythropoietin proteins of formula (III) are represented by the formulae:

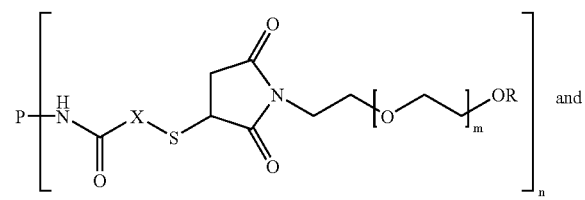

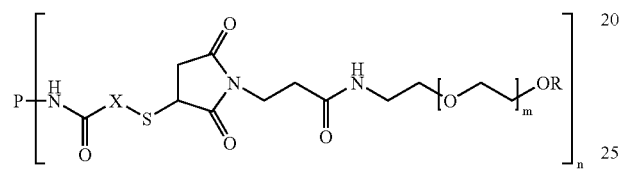

In the most preferred embodiment of the present invention, an erythropoietin conjugate is represented by the formula:

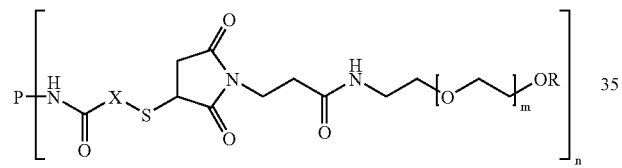

wherein in the above formulae n is an integer from 1 to 3; m is an integer from 450 to 900; R is lower-alkyl; X is —$(CH_2)_k$— or —$CH_2(O—CH_2—CH_2)_k$—, and P is the residue of the erythropoietin protein without the amino group or groups which form an amide linkage with X.

Other preferred erythropoietin glycoprotein products are represented by the formulae:

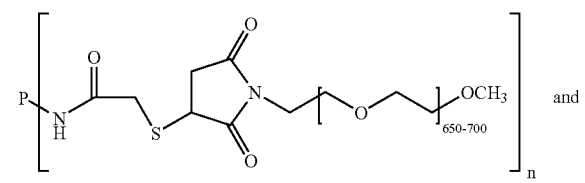

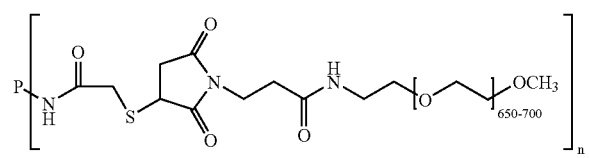

More preferred erythropoietin glycoprotein products are represented by the formula:

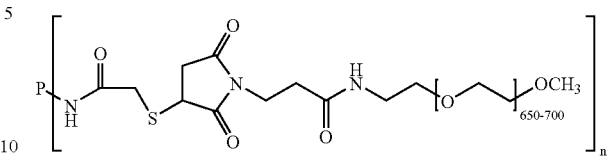

These erythropoietin proteins may be prepared by (a) covalently reacting an ε-amino group of a lysine amino acid of an erythropoietin protein represented by the formula, P—$[NH_2]_n$, with a bi-functional reagent represented by the formula, Z-CO—X—S-Q, to form an intermediate with an amide linkage represented by the formula:

P—$[NH—CO—X—S-Q]_n$ wherein P is an erythropoietin protein less the amino group which forms an amide linkage; n is an integer ranging from 1 to 3; Z is a reactive group, e.g. a carboxylic-NHS ester; X is —$(CH_2)_k$— or —$CH_2(O—CH_2—CH_2)_k$—, wherein k is from 1 to about 10; and Q is a protecting group, like alkanoyl, e.g. acetyl.

(b) covalently reacting the intermediate with an amide linkage from step (a) with an activated poly(ethylene glycol) derivative represented by the formula, W—$[OCH_2CH_2]_m$—OR, to form an erythropoietin glycoprotein product represented by the formula:

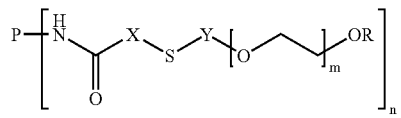

wherein W is a sulfhydryl reactive form of Y; m is an integer ranging from about 450 to about 900; R is lower-alkyl; and Y is as defined above.

In this embodiment, the bi-functional reagent is preferably N-succinimidyl-S-acetylthiopropionate or N-succinimidyl-S-acetylthioacetate, Z is preferably N-hydroxy-succinimide, and the activated poly(ethylene glycol) derivative W—$[OCH_2CH_2]_m$—OR is preferably selected from the group consisting of iodo-acetyl-methoxy-PEG, methoxy-PEG-vinylsulfone, and methoxy-PEG-maleimide.

In more detail, the erythropoietin proteins of formula (III) may be prepared by covalent linking of thiol groups to EPO ("activation") and coupling the resulting activated EPO with a poly(ethylene glycol) (PEG) derivative. The first step for the preparation of pegylated EPO according to the present invention comprises covalent linking of thiol groups via $NH_2$-groups of EPO. This activation of EPO is performed with bi-functional reagents which carry a protected thiol group and an additional reactive group, such as active esters (e.g., a succinimidylester), anhydrides, esters of sulphonic acids, halogenides of carboxylic acids and sulphonic acids, respectively. The thiol group is protected by groups known in the art, e.g., acetyl groups. These bi-functional reagents are able to react with the ξ-amino groups of the lysine amino acids by forming an amide linkage. The first step of the reaction is set out below:

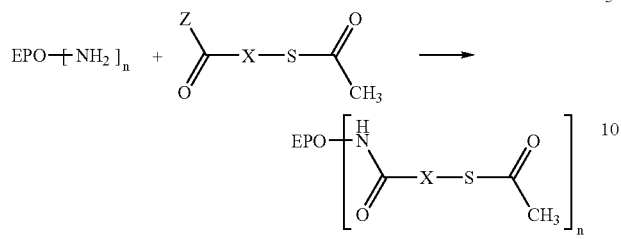

EPO, n and X are as defined above and Z is a reactive group known in the art, e.g. a N-hydroxy-succinimide (NHS) substituent of the formula

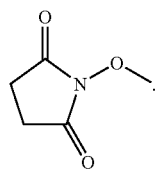

In a preferred embodiment the activation of the ε-amino lysine groups is performed by reaction with bi-functional reagents having a succinimidyl moiety. The bi-functional reagents may carry different spacer species, e.g. $-(CH_2)_k-$ or $-CH_2-(O-CH_2-CH_2-)_k-$ moieties, wherein k is from 1 to about 10, preferably from 1 to about 4, and more preferably 1 or 2, and most preferably 1. Examples of these reagents are N-succinimidyl-S-acetylthiopropionate (SATP) and N-succinimidyl-S-acetylthioacetate (SATA)

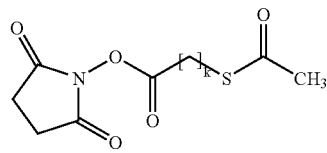

Acetylthioalkyl-carboxylic-NHS-ester, like

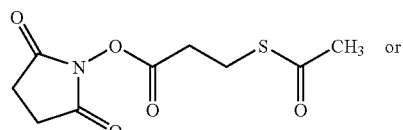

SATP

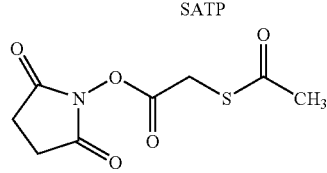

SATA

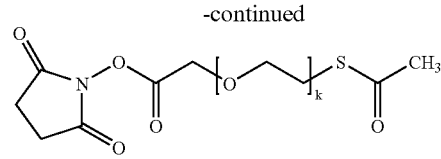

2-(Acetylthio)-(ethoxy)$_k$-acetic-acid-NHS-ester with k as defined above.

The preparation of the bi-functional reagents is known in the art. Precursors of 2-(acetylthio)-(ethoxy)$_k$-acetic-acid-NHS-esters are described in DE-3924705, while the derivatization to the acetylthio compound is described by March, J., Advanced Organic Chemistry, McGraw-Hill, 1977, 375-376. SATA is commercially available (Molecular Probes, Eugene, Oreg., USA and Pierce, Rockford, Ill.).

The number of thiol groups to be added to an EPO molecule can be selected by adjusting the reaction parameters, i.e., the protein (EPO) concentration and the protein/bi-functional reagent ratio. Preferably, the EPO is activated by covalently linking from 1 to 5 thiol groups per EPO molecule, more preferably from 1.5 to 3 thiol groups per EPO molecule. These ranges refer to the statistical distribution of the thiol group over the EPO protein population.

The reaction is carried out, for example, in an aqueous buffer solution, pH 6.5-8.0, e.g., in 10 mM potassium phosphate, 50 mM NaCl, pH 7.3. The bi-functional reagent may be added in DMSO. After completion of the reaction, preferably after 30 minutes, the reaction is stopped by addition of lysine. Excess bifunctional reagent may be separated by methods known in the art, e.g., by dialysis or column filtration. The average number of thiol groups added to EPO can be determined by photometric methods described in, for example, Grasetti, D. R. and Murray, J. F. in J. Appl. Biochem. Biotechnol. 119, 41-49 (1967).

The above reaction is followed by covalent coupling of an activated poly(ethylene glycol) (PEG) derivative. Suitable PEG derivatives are activated PEG molecules with an average molecular weight of from about 20 to about 40 kDa, more preferably from about 24 to about 35 kDa, and most preferably about 30 kDa.

Activated PEG derivatives are known in the art and are described in, for example, Morpurgo, M. et al. J. Bioconj. Chem. (1996) 7, page 363 ff for PEG-vinylsulfone. Linear chain and branched chain PEG species are suitable for the preparation of the compounds of Formula 1. Examples of reactive PEG reagents are iodo-acetyl-methoxy-PEG and methoxy-PEG-vinylsulfone:

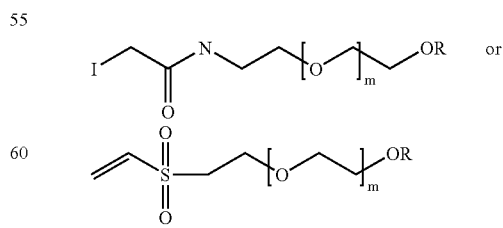

The use of these iodo-activated substances is known in the art and described e.g. by Hermanson, G. T. in Bioconjugate Techniques, Academic Press, San Diego (1996) p. 147-148.

Most preferably, the PEG species are activated by maleimide using (lower-alkoxy-PEG-maleimide), such as methoxy-PEG-maleimide (MW 30000; Shearwater Polymers, Inc.). The structure of lower-alkoxy-PEG-maleimide is as follows:

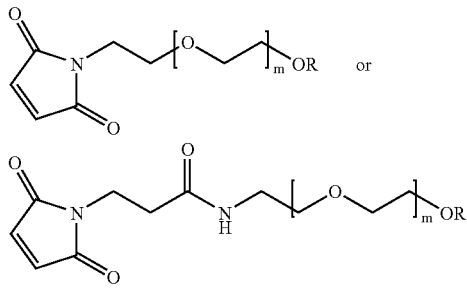

with R and m are as defined above, preferably

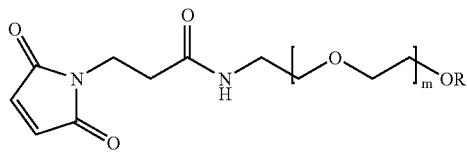

The coupling reaction with lower-alkoxy-PEG-maleimide takes place after in situ cleavage of the thiol protecting group in an aqueous buffer solution, e.g. 10 mM potassium phosphate, 50 mM NaCl, 2 mM EDTA, pH 6.2. The cleavage of the protecting group may be performed, for example, with hydroxylamine in DMSO at 25° C., pH 6.2 for about 90 minutes. For the PEG modification the molar ratio of activated EPO/lower-alkoxy-PEG-maleimide should be from about 1:3 to about 1:6, and preferably 1:4. The reaction may be stopped by addition of cysteine and reaction of the remaining thiol (—SH) groups with N-methylmaleimide or other appropriate compounds capable of forming disulfide bonds. Because of the reaction of any remaining active thiol groups with a protecting group such as N-methylmaleimide or other suitable protecting group, the EPO glycoproteins in the conjugates of this invention may contain such protecting groups. Generally the procedure described herein will produce a mixture of molecules having varying numbers of thiols protected by different numbers of the protecting group, depending on the number of activated thiol groups on the glycoprotein that were not conjugated to PEG-maleimide.

Whereas N-methylmaleimide forms the same type of covalent bond when used to block the remaining thiol-groups on the pegylated protein, disulfide compounds will lead in an intermolecular sulfide/disulfide exchange reaction to a disulfide bridged coupling of the blocking reagent. Preferred blocking reagents for that type of blocking reaction are oxidized glutathione (GSSG), cysteine and cystamine. Whereas with cysteine no additional net charge is introduced into the pegylated protein, the use of the blocking reagents GSSG or cystamine results in an additional negative or positive charge.

The further purification of the compounds of formula (III), including the separation of mono-, di- and tri-pegylated EPO species, may be done by methods known in the art, e.g., column chromatography.

Pegylated erythropoietin derivatives preferably contains at least ninety percent mono-PEG conjugates. Usually mono-PEG conjugates of erythropoietin glycoproteins are desirable because they tend to have higher activity than di-PEG conjugates. The percentage of mono-PNG conjugates as well as the ratio of mono- and di-PEG species can be controlled by pooling broader fractions around the elution peak to decrease the percentage of mono-PEG or narrower fractions to increase the percentage of mono-PEG in the composition. About ninety percent mono-PEG conjugates is a good balance of yield and activity. Sometimes compositions in which, for example, at least ninety-two percent or at least ninety-six percent of the conjugates are mono-PEG species (n equals 1) may be desired. In an embodiment of this invention the percentage of conjugates where n is 1 is from ninety percent to ninety-six percent.

Pharmaceutical compositions comprising pegylated erythropoietin are known in the art and are described e.g. in International patent application WO 01/87329. Compositions may comprise 10 to 10000 µg of an erythropoietin protein per ml as defined above. Preferably, the compositions comprise 10 to 1000 µg, e.g. 10, 50, 100, 400, 800 or 2500 µg per ml. Further, the compositions may comprise 10 µg to 10000 µg erythropoietin protein per ml, 10-200 mmol/l sulfate, 10 to 50 mmol/l phosphate, pH 6.0 to 6.5. This composition may also comprise up to 20 mM methionine, 1-5% of a polyol (w/v), up to 0.1% poloxamer 188 which is commercially available as Pluronic F68 (w/v), and optionally up to 1 mM CaCl$_2$. An example of this composition comprises 10 µg to 10000 µg erythropoietin protein per ml, 40 mmol/l sulfate, 10 mmol/l phosphate, 3% mannitol (w/v), 10 mM methionine, 0.01% pluronic F68 (w/v), pH 6.2. In alternative the composition may comprise 10 µg to 10000 µg erythropoietin protein per ml, 10 to 100 mmol/l NaCl, 10 to 50 mmol/l phosphate pH 6.0 to 7.0, optionally 1-5% (w/v) of a polyol. Further, this composition may comprise up to 20 mM methionine, up to 0.1% pluronic F68 (w/v) and optionally 7.5 µmol/l CaCl$_2$. Specifically, this composition may comprise 10 µg to 10000 µg erythropoietin protein per ml, 100 mmol/l NaCl, 10 mM methionine, 0.01% pluronic F68 (w/v), and 10 mmol/l phosphate, pH 7.0.

The present invention also refers to the above composition comprising 10 µg to 10000 µg erythropoietin protein per ml, 10 to 50 mmol/l arginine, pH 6 to pH 6.5, 10 to 100 mmol/l sodium sulfate. In addition, this composition may comprise up to 20 mM methionine, up to 0.1% poloxamer 188 (w/v), optionally up to 1 mmol/l CaCl$_2$ and optionally 1-5% (w/v) of a polyol. Specifically, this composition may 10 µg to 10000 µg erythropoietin protein per ml, 40 mmol/l arginine, pH 6.2, 30 mmol/l sodium sulfate, 3 % mannitol (w/v), 10 mM methionine, 0.01% pluronic F68 (w/v) and optionally 1 mmol/l CaCl$_2$.

A preferred embodiment of the present invention refers to compositions comprising 10 to 10000 µg/ml erythropoietin, preferably 25 to 2500 µg/ml erythropoietin, and a) 10 mM sodium/potassium phosphate, 100 mM NaCl, pH 7.0 or b) 10 mM sodium phosphate, 120 mM sodium sulfate, pH 6.2 or c) 10 mM sodium phosphate, 40 mM sodium sulfate, 3% mannitol (w/v), pH 6.2 or d) 10 mM sodium phosphate, 40 mM sodium sulfate, 3% mannitol (w/v), 10 mM methionine, 0.01% poloxamer 188 (w/v), pH 6.2 or e) 40 mM arginine, 30 mM sodium sulfate, 3% mannitol (w/v), pH 6.2 or f) 40 mM arginine, 30 mM sodium sulfate, 3% mannitol (w/v), 10 mM methionine, 0.01% pluronic F68 (w/v), pH 6.2.

In the most preferred embodiment, the compositions comprise an amount erythropoietin protein of 50, 100, 400, 800 or 2500 μg/ml. The most preferred compositions comprise either 10 mM sodium phosphate, 40 mM sodium sulfate, 3% mannitol (w/v), 10 mM methionine, 0.01% poloxamer 188 (w/v), pH 6.2 or 40 mM arginine, 30 mM sodium sulfate, 3% mannitol (w/v), 10 mM methionine, 0.01% pluronic F68 (w/v), pH 6.2. Further details of such compositions are known from WO 01/87329.

The invention also relates to a method for treating disturbances of iron distribution in diabetes comprising administration of an effective amount of erythropoietin protein as defined above. Furthermore, the invention relates to a medicament for treating disturbances of iron distribution in diabetes characterized in that it contains an effective amount of erythropoietin protein. The methods of treatment and compositions of the invention are particularly useful in the treatment of non insulin dependant diabetes.

In the treatment of iron disturbances of iron distribution in diabetes, EPO can e.g. be administered at a dosage of 150 U/kg body weight twice a week. The dosage can be varied according to the needs of the individual patient and can also be in a range of e.g. 100 to 200 U/kg. Depending of the half life time of the used EPO derivative, a dose can be administered between e.g. 1 or 3 times per week. Depending on the needs of an individual patient, a physician might also choose a different dosage.

The specific activity of EPO or EPO conjugates in accordance with this invention can be determined by various assays known in the art. The biological activity of the purified EPO proteins of this invention are such that administration of the EPO protein by injection to human patients results in bone marrow cells increasing production of reticulocytes and red blood cells compared to non-injected or control groups of subjects.

The biological activity of the EPO proteins, or fragments thereof, obtained and purified in accordance with this invention can be tested by methods according to Annable, et al., Bull. Wld. Hlth. Org. (1972) 47: 99-112 and Pharm. Europa Spec. Issue Erythropoietin BRP Bio 1997(2). Another biological assay for determining the activity of EPO protein, the normocythaemic mouse assay, is described in the art (e.g. Pharm. Europa Spec. Issue Erythropoietin BRP Bio 1997(2), and the monography of erythropoietin of Ph. Eur. BRP.).

The invention will be better understood by reference to the following examples which illustrate but do not limit the invention described herein.

EXAMPLE

A middle-aged woman suffering from diabetes is checked for disturbances of iron distribution by determination of the following parameters—CRP (C reactive protein), ferritin and soluble transferrin receptor—as described P. Lehmann, M. Volkmann, J. Lotz, A. Baldauf, R. Roeddiger, poster presented at the AACC/CSCC, Annual Meeting, Jul. 29-Aug. 2, 2001, Chicago, Ill. The results show disturbances of iron distribution. The patient is treated subcutaneously with 150 U/kg Recormon™ (commercially available erythropoietin protein) twice a week for a maximum of 12 weeks. Afterwards, determination of the parameters as described above shows an improvement of the disorder of iron deficiency.

The invention claimed is:

1. A method of treating disturbances in iron distribution in a patient suffering from non-insulin dependent diabetes mellitus comprising administering to a patient suffering from non-insulin dependent diabetes and disturbances in iron distribution, a therapeutically effective amount of human erythropoietin protein having the amino acid sequence of SEQ ID NO:1 sufficient to treat said disturbances in iron distribution without administering iron.

2. A method of treating disturbances in iron distribution in a patient suffering from non insulin dependent diabetes mellitus comprising administering a therapeutically effective amount of human erythropoietin protein having the amino acid sequence of SEQ ID NO:1 modified by the addition of up to 3 glycosylation sites, wherein the modification is selected from the group consisting of:

$Asn^{30}Thr^{32}$;
$Asn^{51}Thr^{53}$;
$Asn^{57}Thr^{59}$;
$Asn^{69}$;
$Asn^{69}Thr^{71}$;
$Ser^{68}Asn^{69}Thr^{71}$;
$Val^{87}Asn^{88}Thr^{90}$;
$Ser^{87}Asn^{88}Thr^{90}$;
$Ser^{87}Asn^{88}Gly^{89}Thr^{90}$; (SEQ ID NO: 2);
$Ser^{87}Asn^{88}Thr^{90}Thr^{92}$;
$Ser^{87}Asn^{88}Thr^{90}Ala^{162}$;
$Asn^{69}Thr^{71}Ser^{87}Asn^{88}Thr^{90}$;
$Asn^{30}Thr^{32}Val^{87}Asn^{88}Thr^{90}$;
$Asn^{89}Ile^{90}Thr^{91}$;
$Ser^{87}Asn^{89}Ile^{90}Thr^{91}$;
$Asn^{136}Thr^{138}$;
$Asn^{138}Thr^{140}$;
$Thr^{125}$; and
$Pro^{124}Thr^{125}$.

3. A method of treating disturbances in iron distribution in a patient suffering from non insulin dependent diabetes mellitus comprising administering a therapeutically effective amount of human erythropoietin protein, without administering iron, wherein the protein (EPO) is an analog of SEQ ID NO:1, said analog is selected from the group consisting of: (a) human erythropoietin protein having the amino acid sequence, Ser Ser Ser Ser Lys Ala Pro Pro Pro Ser Leu Pro Ser Pro Ser Arg Leu Pro Gly Pro Ser Asp Thr Pro Ile Leu Pro Gln (SEQ ID NO: 3), extending from the cathoxy terminus; (b) the analog in (a) further comprising $Ser^{87}$ $Asn^{88}$ $Thr^{90}$ EPO; (c) the analog in (a) further comprising $Asn^{30}$ $Thr^{32}$ $Val^{87}$ $Asn^{88}$ $Thr^{90}$ EPO; (d) the analog in (a) further comprising $Gln^{24}$ $Ser^{87}$ $Thr^{88}$ $Thr^{90}$ EPO; (e) the analog in (a) further comprising $Gln^{38}$ $Ser^{87}$ $Asn^{88}$ $Thr^{90}$ EPQ; (f) the analog in (a) further comprising $Gln^{83}$ $Ser^{87}$ $Asn^{88}$ $Thr^{90}$ EPO and (g) darbepoetin alfa.

4. The method of claim 1, wherein the erythropoietin protein is pegylated.

5. A method of treating disturbances m iron distribution in a patient suffering from non-insulin dependent diabetes mellitus comprising administering a conjugate of human erythropoietin protein of SEQ ID NO:1, wherein said conjugate comprising the erythropoietin protein of SEQ ID NO:1 having one to three free amino groups covalently linked to n poly(ethylene glycol) groups of the formula —CO—$(CH_2)_x$—$(OCH_2CH_2)_m$—OR with the —CO of each poly(ethylene glycol) group forming an amide bond with one of said amino groups; wherein R is a lower-alkyl; x is 2 or 3; in is from about 450 to about 900; n is from 1 to 3; and n and in are chosen so that the molecular weight of the conjugate minus the erythropoietin protein is from 20 kilodaltons to 100 kilodaltons.

6. The method of claim 5, wherein x is 3, in is 650 to 750, n is 1 and R is methyl.

7. The method of claim 5 wherein the conjugate has the formula

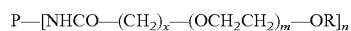

P—[NHCO—$(CH_2)_x$—$(OCH_2CH_2)_m$—OR]$_n$ wherein P is the residue of the protein without the free amino group that forms the amide linkage;

R is lower alkyl;

x is 2 or 3;

m is from about 450 to about 900;

n is from 1-3; and wherein m and n are selected such that the molecular weight of the conjugate minus the erythropoietin protein is from about 20 kD to about 100 kD.

8. A method of treating disturbances in iron distribution in a patient suffering from non-insulin dependent diabetes mellitus comprising administering a conjugate of human erythropoietin of SEQ ID NO:1 wherein, said conjugate comprises the erythropoietin protein of SEQ ID NO:1 having one to three free amino groups covalently linked to the erythropoietin protein via a linker of the formula —C(O)—X—S—Y— with the C(O) of the linker forming an amide bond with one of said amino groups, X is —$(CH_2)_k$— or $CH_2(O—CH_2—CH_2)_k$—, k is from 1 to 10, Y is

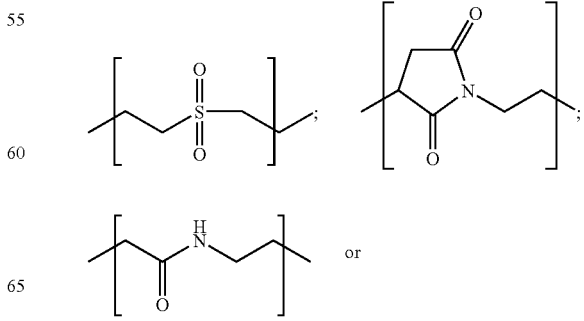

-continued

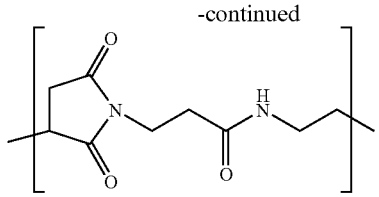

the average molecular weight of each poly(ethylene glycol) moiety is from about 20 kilodaltons to about 40 kilodaltons, and the molecular weight of the conjugate is from about 51 kilodaltons to about 175 kilodaltons.

9. The method of claim 8, wherein the conjugate has the formula:

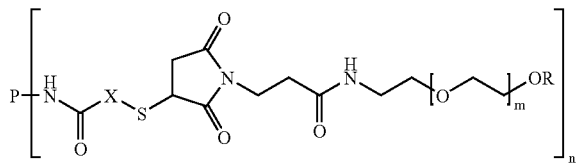

wherein n is an integer from 1 to 3; in is an integer from 450 to 900; R is lower-alkyl; X is —(CH$_2$)$_k$— or —CH$_2$(O—CH$_2$—CH$_2$)$_k$—, k is 1 to 10 and P is the residue of the erythropoietin protein without the n amino groups which form an amide linkage with X.

10. A composition for the treatment of disturbances in iron distribution comprising from about 25 to about 2,500 μg/ml of erythropoietin protein, from about 10 to about 200 mmol/l sulfate, a pharmaceutically acceptable carrier, wherein said composition has a pH of from about 6.0 to about 7.0.

11. The composition of claim 10 comprising from about 50 to about 2,500 μg/ml of erythropoietin protein, 10 mm sodium phosphate, 40 mM sodium sulfate, 3% mannitol (w/v), 10 mM metihionine and 0.01% poloxamer 188 (w/v) and has a pH of about 6.2.

12. The composition of claim 10 comprising from about 50 to about 2,500 μg/ml of erythropoietin protein, 40 mM arginine, 30 mM sodium sulfate, 3% mannitol (w/v), 10 mM methionine, 0.01% poloxamer 188 (w/v) and having a pH of about 6.2.

13. A method of treating disturbances in iron distribution in a patient suffering from diabetes comprising administering a therapeutically effective amount of a composition of human erythropoietin protein of SEQ ID NO:1, wherein the composition comprises from about 25 to about 2,500 μg/ml of erythropoietin protein, from about 10 to about 200 mmol/l sulfate and having a pH of from about 6.0 to about 7.0.

14. A method of treating disturbances in non distribution in a patient suffering from diabetes comprising administering a therapeutically effective amount of a composition of human erythropoietin protein of SEQ ID NO:1 modified by the addition of up to 3 glycosylation sites, wherein the composition comprises from about 25 to about 2,500 μg/ml of erythropoietin protein, from about 10 to about 200 mmol/l sulfate and having a pH of from about 6.0 to about 7.0.

15. The method of claim 13, wherein the erythropoietin protein is pegylated.

16. A method of treating disturbances in iron distribution in a patient suffering from diabetes comprising administering a composition of a conjugate of human erythropoietin protein of SEQ ID NO:1, wherein said conjugate comprises the erythropoietin protein of SEQ ID NO:1, having one to three free amino groups being covalently linked to n poly(ethylene glycol) groups of the formula —O—(CH$_2$)$_x$—(OCH$_2$CH$_2$)$_m$—OR with the —CO of each poly(ethylene glycol) group forming an amide bond with cine of said amino groups; wherein R is a lower-alkyl; x is 2 or 3; m is from about 450 to about 900; n is from, 1 to 3; and n and m are chosen so that the molecular weight of the conjugate minus the erythropoietin protein is from 20 kilodaltons to 100 kilodaltons, wherein said composition comprises from about 25 to about 2500 ug/ml of erythropoietin protein, from about 10 to about 200 mmol/l sulphate and having a pH of from about 6.0 to about 7.0.

17. The method of claim 16, wherein x is 3, m is 650 to 750, n is 1 and R is methyl.

18. The method of claim 16, wherein the conjugate has the formula

P—[NHCO—(CH$_2$)$_x$—(OCH$_2$CH$_2$)$_m$—OR]$_n$ wherein P is the residue of the protein without the free amino group tat forms the stride linkage;

R is lower alkyl;

x is 2or 3;

m is from about 450to about 900;

n is from 1-3; and wherein in and n are selected such that the molecular weight of the conjugate minus the erythropoietin protein is from about 20 kD to about 100 kD.

19. A method of treating disturbances in iron distribution in a patient suffering from diabetes comprising administering a composition of a conjugate of human erythropoietin protein of SEQ ID NO:1, wherein said conjugate the erythropoietin protein of SEQ ID NO:1 having one to three free amino groups covalently linked to from one to three lower-alkoxy poly(ethylene glycol) groups, each poly(ethylene glycol) group being covalently linked to the eryhropoietin protein via a linker of the formula—C(O)—X—S—Y—with the C(O) of the linker forming ah amide bond with one of said amino groups, X is —(CH$_2$)$_k$— or —CH$_2$(O—CH$_2$—CH$_2$)$_k$—, k is from 1 to 10, Y is

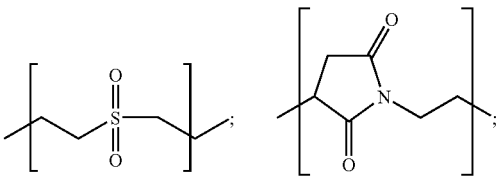

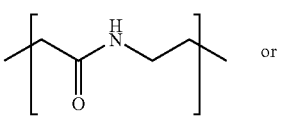 or

-continued

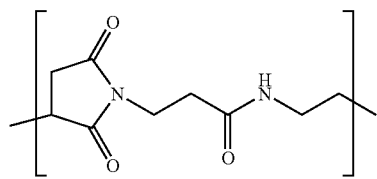

wherein the average molecular weight of each poly(ethylene glycol) moiety is from about 20 kilodaltons to about 40 kilodaltons, and the molecular weight of the conjugate is from about 51 kilodaltons to about 175 kilodaltons wherein said composition comprises from about 25 to about 2500 ug/ml of erythropoietin protein, from about 10 to about 200 mold sulfate and having a pH of from about 6.0 to about 7.0.

20. The method of claim 19, wherein the conjugate has the formula:

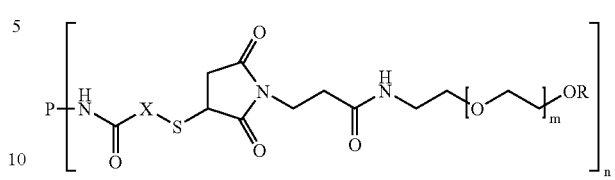

wherein a is an integer from i to 3; m is an integer from 450 to 900; R is lower-alkyl; X is —$(CH_2)_k$— or —$CH_2$)O—$CH_2$—$CH_2)_k$—, k is 1 to 10 and P is the residue of the erythropoietin protein without the a amino groups which form an amide linkage with X.

* * * * *

SEQUENCE LISTING

<160> NUMBER OF SEQ ID NOS: 1

<210> SEQ ID NO 1
<211> LENGTH: 165
<212> TYPE: PRT
<213> ORGANISM: Homo sapiens

<400> SEQUENCE: 1

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
```

```
                130              135              140
Tyr Ser Asn Phe Leu Arg Gly Lys Leu Lys Leu Tyr Thr Gly Glu Ala
145                  150              155              160

Cys Arg Thr Gly Asp
                165
```